United States Patent [19]

Rosenberg

[11] Patent Number: 5,071,409
[45] Date of Patent: Dec. 10, 1991

[54] VACUUM DEVICE PARTICULARLY USEFUL FOR DRAINING WOUNDS

[76] Inventor: Lior Rosenberg, 4 Ophir St., Tel Baruch, Tel Aviv, Israel

[21] Appl. No.: 637,034
[22] Filed: Jan. 3, 1991

[30] Foreign Application Priority Data

Jan. 12, 1990 [IL] Israel .................................. 93045

[51] Int. Cl.⁵ ........................... A61M 1/00; A61B 5/14
[52] U.S. Cl. ..................................... 604/119; 128/766; 604/133; 604/187
[58] Field of Search ............... 604/119, 133, 134, 146, 604/149, 121, 73, 118, 187; 128/765, 766

[56] References Cited

U.S. PATENT DOCUMENTS

| | | | |
|---|---|---|---|
| 2,594,621 | 4/1952 | Derrick | 128/765 |
| 4,215,702 | 8/1920 | Ayer | 128/766 |
| 4,319,582 | 3/1982 | Eldridge | 128/766 |
| 4,340,068 | 7/1962 | Kaufman | 128/768 |
| 4,403,987 | 9/1983 | Gottinger | 604/134 |
| 4,578,060 | 3/1986 | Huck et al. | 604/133 |
| 4,664,128 | 5/1987 | Lee | 604/187 |
| 4,838,855 | 6/1989 | Lynn | 128/765 |
| 4,966,585 | 10/1990 | Gangemi | 604/134 |

FOREIGN PATENT DOCUMENTS 32826 7/1981 European Pat. Off. ............ 604/121

Primary Examiner—Paul J. Hirsch
Attorney, Agent, or Firm—Benjamin J. Barish

[57] ABSTRACT

A vaccum device includes a cylinder, a plunger receivable through the open end of the cylinder and having a piston movable within the cylinder to define a suction chamber; and indicia carried by the cylinder cooperable with a reference on the plunger for providing a visual indication of the suction in the suction chamber. The indicia is in the form of a curve representing the variation of pressure in the suction chamber with the volume of the chamber as indicated by a reference on the piston.

17 Claims, 3 Drawing Sheets

VACUUM DEVICE PARTICULARLY USEFUL FOR DRAINING WOUNDS

FIELD AND BACKGROUND OF THE INVENTION

The present invention relates to a vacuum-producing device for evacuating enclosures. The invention also relates to a holder and to a collection bag particularly useful with the novel vacuum-producing device. The vacuum-producing device, holder and collection bag of the present invention are particularly useful for draining wounds, and are therefore described below with respect to this application.

It is generally recognized that the healing of a wound may be greatly promoted by providing drainage of the fluids that accumulate within the wound. A number of devices have been used for this purpose, including simple rubber tubes and capillary tubes. Such draining arrangements, however, are slow-acting since they operate by natural pressure differences or by capillary action to produce the drainage. Other known devices include active vacuum-producing arrangements, but these are usually of complicated and/or bulky construction, and are therefore not generally feasable for use with certain types of wounds, such as those resulting fron plastic surgery, wherein the quantity of fluids to be drained is relatively small and the vacuum needed is high.

OBJECTS AND BRIEF SUMMARY OF THE INVENTION

An object of the present invention is to provide a vacuum device of the latter type particularly useful for draining wounds and having a number of improvements as will be described more particularly below.

According to the present invention, there is provided a vacuum device conectible to a suction line for applying suction to an object, comprising: a cylinder open at one end and closed at its opposite end by an end wall formed with a passageway therethrough; a plunger receivable through the open end of the cylinder and having a piston movable within the cylinder towards and away from the end wall to define therewith a suction chamber communicating with the passageway; a spring urging the plunger and its piston away from the end wall to expand the chamber and thereby to produce a negative pressure therein; a valve operable to selectively apply suction from the suction chamber to the suction line when connected to the vacuum device; and indicia carried by the cylinder cooperable with a reference on the plunger for providing a visual indication of the suction applied by the suction chamber to the suction line.

Such a vacuum device thus provides a continuous visual indication of the magnitude of the vacuum applied to the object, e.g., a wound to be drained.

According to a further features in the preferred embodiment of the invention described below, the plunger includes a position sensor cooperable with an electrical element carried by the cylinder for providing an electrial signal when the plunger moves to a point representing a predetermined minimum pressure in the suction chamber. In the described embodiment, the position sensor is a magnetic core carried by the plunger, and the electrical element is an electrical coil carried by the cylinder and electromagnetically coupled to the magnetic core. The electrical coil is manually presettable along the cylinder to manually preset the determined minimum pressure to produce the electrical signal.

According to another aspect of the invention, the vacuum device further includes a holder having mounting means for mounting the cylinder thereon; mounting means for mounting the holder to the object to be subjected to suction for evacuating fluids therefrom; and further mounting means for mounting a collection receptacle thereon to receive the fluids when discharged via the fluid discharge line.

The invention also provides a holder in the form of a carrier plate having releasable retainer means on one side for mounting the cylinder thereon. The releasable retainer means is at one end of the carrier plate, and the carrier plate includes a three-way stop-cock at its opposite end. The one end of the carrier plate includes an end wall bent out of the plane of the remainder of the carrier plate and formed with a recess of substantially the same diameter as the cylinder and constituting the retainer means for releasably retaining the cylinder. The carrier plate is also formed with a pair of openings adjacent the end wall and on opposite sides of the recess for receiving the fingers of the operator when moving the plunger when pressing the thumb against the plunger.

According to a further aspect of the invention, there is provided a collection bag particularly for use with the above vacuum device and holder, the collection bag being of pliable plastic material and including an attachment fixed to one end thereof and formed with an opening for receiving a discharge tube carried by the holder, the stiff attachment member further including a one-way valve permitting flow of fluid only from the discharge line of the holder into the collection bag.

Further features and advantages of the invention will be apparent from the description below.

BRIEF DESCRIPTION OF THE DRAWINGS

The invention is herein described, by way of example only, with reference to the accompanying drawings, wherein.

DESCRIPTION OF A PREFERRED EMBODIMENT

Figure 1:
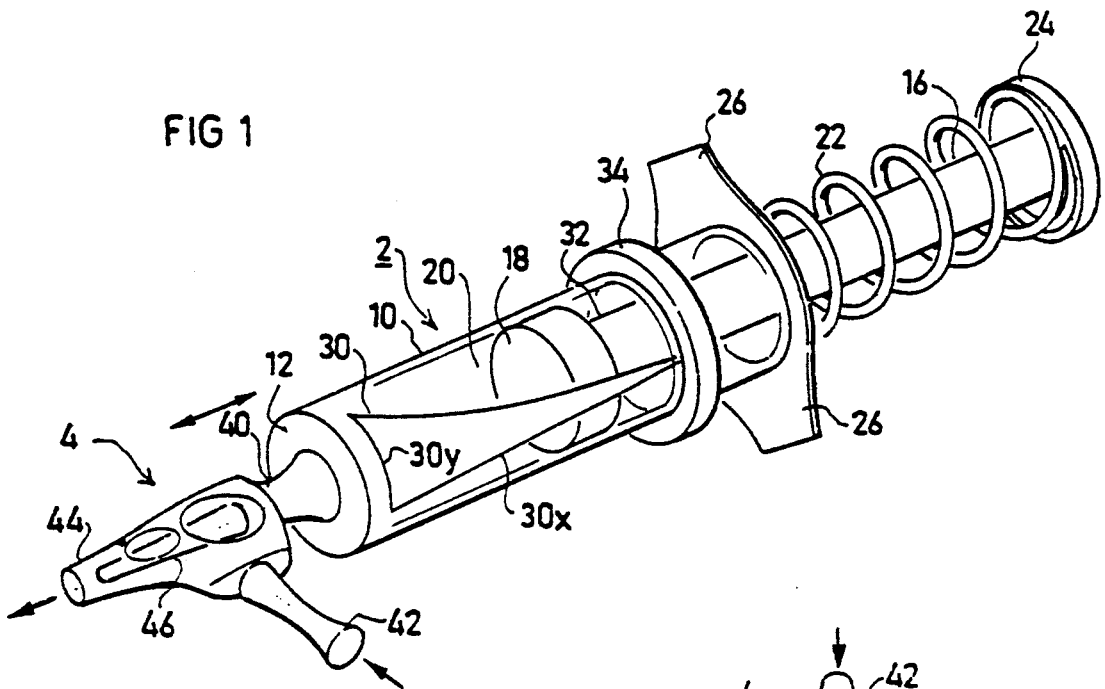
FIG. 1 illustrates one form of vacuum device constructed in accordance with the present invention.

The vacuum device illustrated in the drawings is particularly useful for draining fluids from a wound in order to promote healing of the wound. Broadly, it includes an assembly comprising: a syringe-type vacuum device, generally designated 2 in FIG. 1; a three-way valve assembly such as a three-way stop-cock, generally designated 4 in FIG. 1; a holder, generally designated 6 in FIGS. 3–5, 7 and 8, for mounting the vacuum device and valve assembly; and a collection bag, generally designated 8 in FIGS. 6–8, for collecting the fluids drained from the wound.

More particularly, the syringe-type vacuum device 2 illustrated in FIG. 1 comprises a cylinder 10 open at one end and closed at its opposite end by an end wall 12 formed with a passageway through a connector 14; and a plunger 16 receivable through the open end of cylinder 10 and having a piston 18 movable within the cylinder towards and away from end wall 12 to define an expansible-contractible chamber 20 communicating with the passageway through connector 14. A spring 22 is interposed between the englarged head 24 of plunger 16 and a pair of finger-engaging projections 26 fixed to the open end of cylinder 10. Spring 22 urges the plunger outwardly such that its piston 18 is urged away from end wall 12, thereby expanding chamber 20 and producing a negative pressure therein. This negative pressure is communicated via the passageway within connector 14 and the three-way valve assembly 4 to a suction line (not shown) leading to the wound to be drained.

Cylinder 10, of transparent material, is provided with indicia in the form of a curve 30 cooperable with a reference carried by piston 18 of the plunger 16 for providing a visual indication of the suction applied by chamber 20 to the suction line connected to connector 14. The magnitude of the pressure within chamber 20 is thus represented by the coordinate $30y$ of curve 30, with respect to the displacement of piston 18 represented by coordinate $30x$. The reference carried by piston 18 cooperable with curve 30 is preferably the inner edge of the piston, but may be any reference mark applied to the piston.

Plunger 16 further includes a position sensor for sensing the position of piston 18 within cylinder 10, and thereby the pressure within chamber 20. In the described embodiment, the position sensor is in the form of a magnetic core 32 caried by plunger 16 and cooperable with an electrical coil 34 carried by the outer face of cylinder 10, for providing an electrical signal when the plunger moves to a point representing a predetermined minimum pressure within suction chamber 20. The electrical coil 34 is magnetically coupled to core 32 within cylinder 10 and may be manually preset to any position along the cylinder in order to manually preset the predetermined minimum pressure to produce the electrical signal. The electrical signal so produced may be used for actuating an indicator or alarm in order to alert an attendant that the suction within the chamber 20 has reached a predetermined minimum value.

Figure 2:
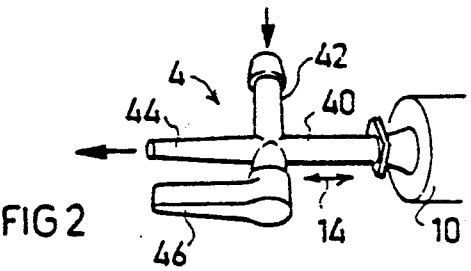
FIG. 2 more particularly illustrates an optional three-way valve included in the vacuum device of FIG. 1.

The three-way valve assembly 4 illustrated in FIGS. 1 and 2 includes three connectors or ports 40, 42, 44, controlled by a valve operator 46. Port 40 of the stopcock is connected to passageway 14 leading to the suction chamber 20; port 42 is adapted to receive the suction line (not shown) leading to the wound to be drained for applying suction thereto; and port 44 is adapted to be connected to a discharge line for discharging the fluid accumulating within chamber 20 into a collection receptacle. Thus, when operator 46 is aligned with port 40, the suction chamber 20 is closed; when it is aligned with port 42, the suction chamber is connected to the suction line for applying suction to the wound, and thereby for drawing the fluid from the wound into suction chamber 20; and when operator 46 is aligned with port 44, the suction chamber is connected to the discharge line enabling the fluid accumulating within chamber 20 to be discharged by pressing plunger 16 inwardly into its cylinder 10. Where a three-way valve is used, port 42 is connected to the drainage line and allows movement of fluids only towards the syringe. Port 44 connected to the collection receptacle allows fluid to move only towards the receptacle and prevents backflow towards the syringe or line.

Figure 8:
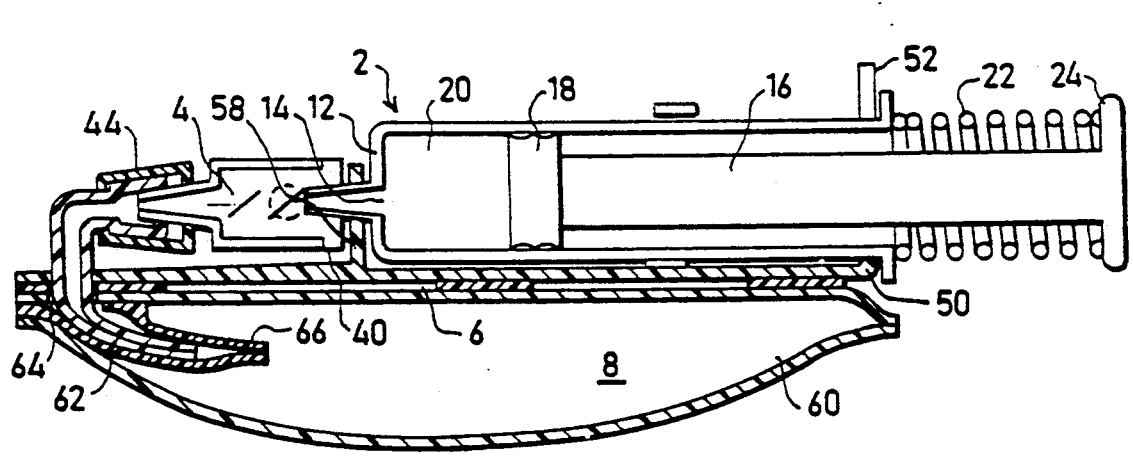
FIGS. 7 and 8 are end and longitudinal sectional views, respectively, illustrating the assembly of FIG. 3.
Figure 6:
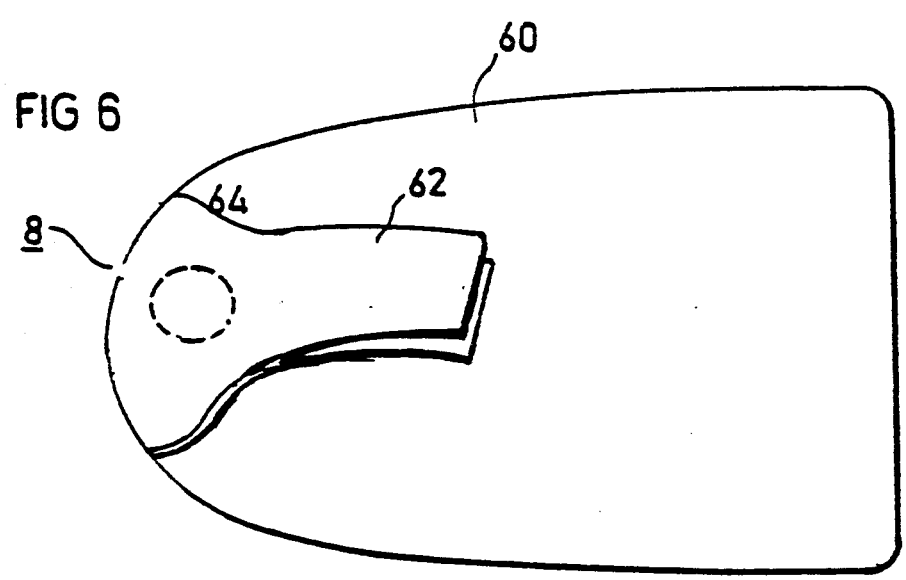
FIG. 6 illustrates the collection bag used in the assembly of FIG. 3.
Figure 7:
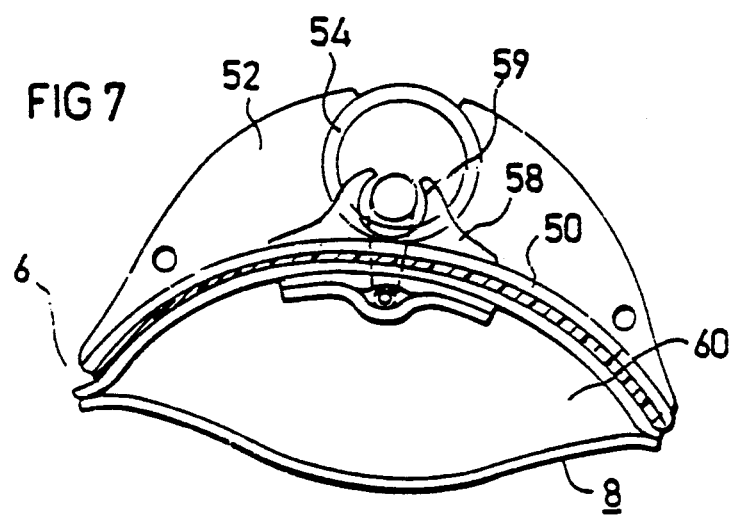

The suction device 2, and the three-way stop-cock 4, as well as a collection receptacle shown at 8 in FIGS. 6–8, may be mounted on holder 6 to provide a compact, convenient assembly for use in draining wounds.

Thus, as shown particularly in FIGS. 3–5 and 8, holder 6 includes a carrier plate 50 having an end wall 52 bent substantially perpendicularly to the remainder of carrier plate and formed with a semicircular recess 54 for removably receiving cylinder 10 of the vacuum-device 2. Plate 50 is formed with a pair of openings 56 adjacent to its end wall 52 and on opposite sides of recess 54. Openings 56 are adapted to receive the operator's fingers when applying pressure by the thumb against head 24 of plunger 16 in order to move the plunger within the cylinder 10. Plate 50 is further formed with an upstanding wall 58 including a semi-circular recess 59 for removably receiving connector 14.

The three-way valve assembly 4 described above, particularly with respect to FIGS. 1 and 2, is fixed to the opposite end of the carrier plate 50, such that its connector port 40 receives connector 14 of the cylinder and thereby firmly secures that end of the valve assembly to the carrier plate. Connector port 44 of the three-way valve assembly 4 includes, or is in the form of, a rigid tube passing around the carrier plate 50, or through an opening formed in the carrier plate, so as to communicate with the collection receptacle 8 carried by the underside of the carrier plate 50.

Figure 5:
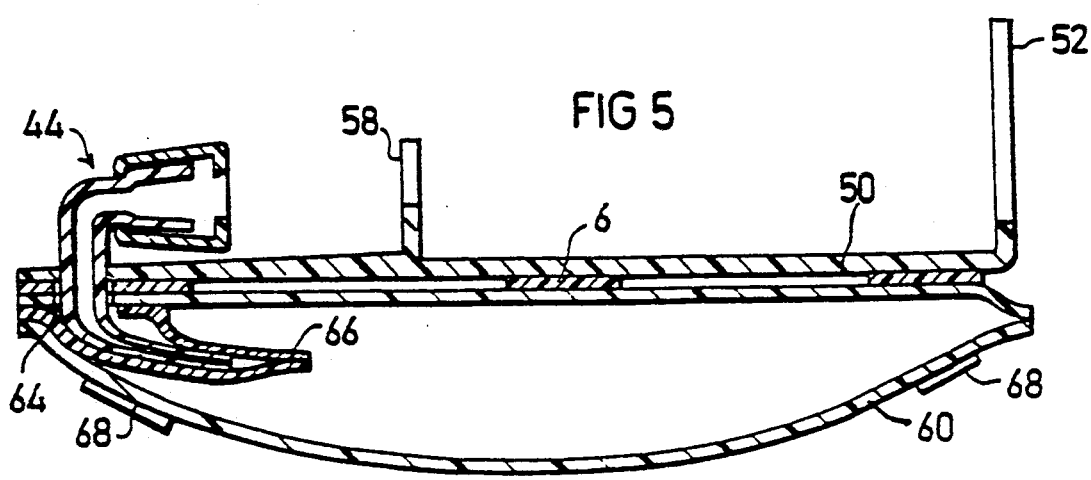

Collection receptacle 8 is in the form of a pliable plastic bag 60 having a stiff insert 62 extending from its upper face and formed with an opening 64 for receiving the rigid tube of connector port 44 of the three-way cock-stop 4. As shown in FIG. 5, the stiff insert 62 extends within the pliable bag 60 and is formed with a one-way leaf valve 66, which permits the fluid to flow only into the collection bag 60. The collection bag 8 may be secured to the underside of carrier plate 50 by any suitable means, such as by straps 68, or adhesive tape, with or without the assistance of rigid tube connector port 44.

Figure 3:
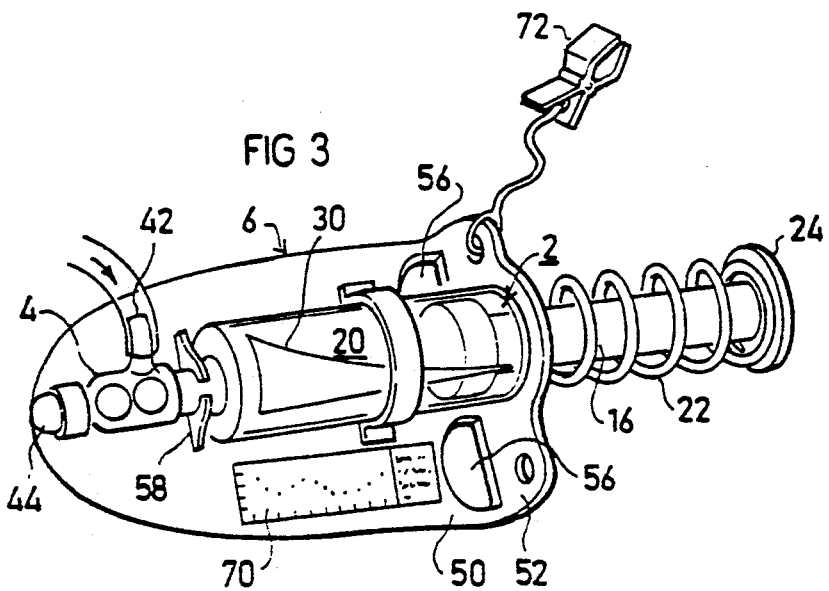
FIG. 3 illustrates an assembly including the vacuum device of FIG. 1 together with a holder for mounting to an object to be subjected to the vacuum.
Figure 4:
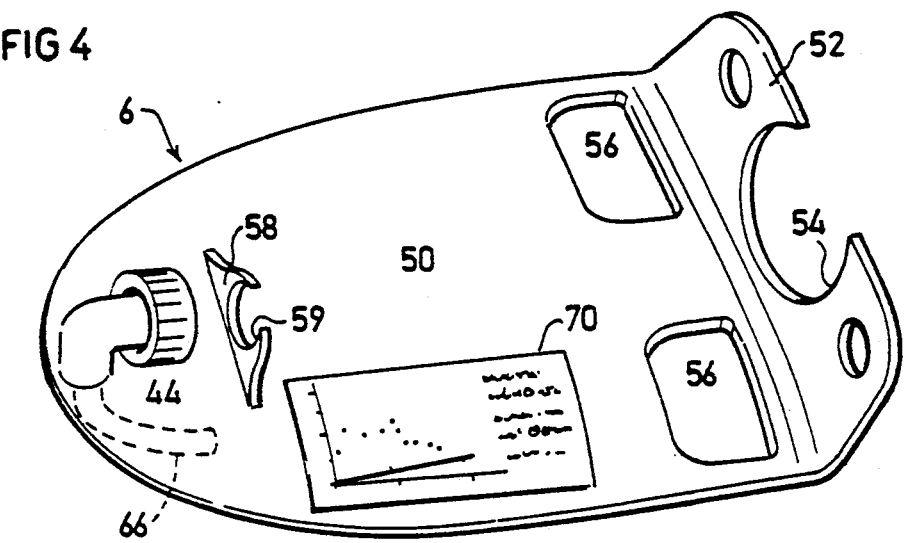
FIGS. 4 and 5 are perspective and longitudinal sectional views, respectively, illustrating the holder alone used in the assembly of FIG. 3.

As shown in FIG. 3, holder 6 further includes a table for applying a chart 70 which may be used for charting the amount of drained fluid discharged from the suction chamber 20 into the collection bag 60, to thereby enable an attendant to be containuously apprised of the rate of accumulation of such fluid.

Holder 6 further includes a clip 72 for attaching the carrier plate, together with the vacuum-device 2 carried on one side, and the collection bag 8 carried on the opposite side, to the garment or dressing of a subject having the wound to be drained.

The device illustrated in the drawings may be used in the following manner in order to drain the wound resulting, e.g., from a plastic surgery operation.

The vacuum device 2 is mounted to one side of holder 6 by pressing cylinder 10 into the semicircular recess 54 formed in end wall 52 of the carrier plate, and by inserting the connector 14 at the end of the cylinder into port 40 of the three-way stop-cock 4. A collection bag 8 is then applied to the underface of the carrier plate by the straps 68 and by inserting the rigid discharge port 44 of the three-way valve assembly 4 into opening 64 formed in the collection bag. Coil 34 is then preset to fix a minimum pressure when a signal or alarm is to be actuated.

Where the three-way valve 4 is a stop-cock, its operator 46 is then moved to connect port 40 to port 42; and plunger 16 is depressed so as to contract chamber 20 within cylinder 10. Operator 46 of the stop-cock is then moved to close port 40, and the plunger is released, whereupon the spring 22 moves the plunger outwardly, thereby expanding chamber 20 and producing a negative pressure therein. When the three-way valve assembly uses check valves (one-way valves), the operator has only to press in the plunger.

A suction line is then applied at one end to connector port 42, and at its opposite end to the wounds to be drained. Operator 46 is then moved to connect port 40 to port 42, whereby the suction within chamber 20 is now applied via the suction tube to the wound to be drained.

The amount of suction applied to the wound is indicated by the position of piston 18 with respect to curve 30. The fluid is drawn into chamber 20 as piston 18 moves outwardly of the chamber, thereby decreasing the pressure within the chamber as indicated by curve 30. The vacuum within chamber 20 is sensed by core 32 carried by plunger 16 movable with respect to coil 34 carried by cylinder 10. The latter coil outputs an electrical signal when a predetermined minimum vacuum has been reached, which signal may be used to energize an indicator or alarm for alerting the attendant.

Chamber 20 may be periodically drained by moving operator 46 to connect the discharge port 44 to port 40, and then to press plunger 24 inwardly into cylinder 10. If check vales are used, the operator need only press in the plunger. The fluids are thus discharged via port 44 and the discharge tube received within opening 64 formed in the collection bag 8 at the underside of the carrier plate 50. The amount of fluid so discharged may be recorded on chart 70.

While the invention has been described with respect to one preferred embodiment, it will be appreciated that many variations, modifications and other applications of the invention may be made.

What is claimed is:

1. A vacuum device connectible to a suction line for applying suction to an object, comprising:
   a cylinder open at one end and closed at its opposite end by an end wall formed with a passageway therethrough;
   a plunger receivable through the open end of the cylinder and having a piston movable within the cylinder towards and away from said end wall to define therewith a suction chamber communicating with said passageway;
   a spring urging said plunger and its piston away from said end wall to expand said chamber and thereby to produce a negative pressure therein;
   a valve operable to selectively apply suction from said suction chamber to said suction line when connected to said vacuum device;
   and indicia carried by said cylinder cooperable with a reference on said plunger for providing a visual indication of the suction applied by said suction chamber to the suction line.

2. The vacuum device according to claim 1, wherein said indicia is in the form of a curve representing the variation of pressure in said suction chamber with the volume of said chamber as indicated by said reference on said plunger.

3. The vacuum device according to claim 1, wherein said plunger includes a position sensor cooperable with an electrical element carried by said cylinder for providing an electrial signal when the plunger moves to a point representing a predetermined minimum pressure in said suction chamber.

4. The vacuum device according to claim 3, wherein said position sensor is a magnetic core carried by said plunger, and said electrical element is an electrical coil carried by said cylinder and electromagnetically coupled to said magnetic core.

5. The vacuum device according to claim 4, wherein said electrical coil is manually presettable along said cylinder to manually preset said determined minimum pressure to produce said electrical signal.

6. The vacuum device according to claim 1, wherein said valve includes an assembly comprising:
   a first port connected to said passageway through the cylinder end wall;
   a second port connectible to said suction line;
   a third port connectible to a fluid-discharge line;
   and an operator selectively positionable to a suction position to connect the first port to the second port and thereby to apply the suction of said chamber to said suction line, or to a discharge position to connect the first port to the third port and thereby to permit the fluid accumulated in said chamber to be discharged via said fluid discharge line by manually moving said plunger towards said cylinder end wall.

7. The vacuum device according to claim 6, wherein said valve assembly comprises check valves.

8. The vacuum device according to claim 1, further including a holder having:
   first mounting means for mounting said cylinder thereon;
   and second mounting means for mounting a collection receptacle thereon to receive the fluids when discharged via said fluid discharge line.

9. The vacuum device according to claim 8, wherein said valve is included in a stop-cock carried by said holder.

10. The vacuum device according to claim 8, wherein said holder is in the form of a carrier plate having releasable retainer means on one side thereof, constituting said first mounting means, for mounting said cylinder thereon.

11. The vacuum device according to claim 10, wherein said releasable retainer means is at one end of the carrier plate, said valve being included in a three-way valve assembly carried at the opposite end of said carrier plate.

12. The vacuum device according to claim 11, wherein said one end of the carrier plate includes an end wall bent out of the plane of the remainder of the carrier plate and formed with a recess of substantially the same diameter as said cylinder and constituting said retainer means for releasably retaining said cylinder.

13. The vacuum device according to claim 12, wherein said carrier plate is formed with a pair of openings adjacent said end wall and on opposite sides of said recess for receiving the fingers of the operator when moving said plunger by pressing the thumb against said plunger.

14. The vacuum device according to claim 11, further including a clip for mounting the carrier plate to the object to be subjected to said suction.

15. The vacuum device according to claim 11, in combination with a collection bag, constituting said collection receptacle, mounted to said carrier plate by said second mounting means, said carrier plate including a tube fixed to said three-way valve assembly and constituting said discharge line connectible to said collection bag.

16. The vacuum device according to claim 15, wherein said collection bag is made of pliable plastic material and includes an attachment member fixed thereto and formed with an opening for receiving said tube of the three-way valve assembly, said fixed attachment member being further formed with a one-way valve permitting the flow of fluid only from said tube into said collection bag.

17. The vacuum device according to claim 8, wherein said holder further includes means for mounting a chart thereon for recording the quantities of fluid discharged into said collection receptacle.

* * * * *